US005722935A

United States Patent [19]
Christian

[11] Patent Number: 5,722,935
[45] Date of Patent: Mar. 3, 1998

[54] LAPAROSCOPIC RETRACTOR HAVING A PLURALITY OF BLADES EXTENDING LATERALLY FROM A HANDLE

[75] Inventor: Steven C. Christian, New Brighton, Minn.

[73] Assignee: Minnesota Scientific, Inc., Minneapolis, Minn.

[21] Appl. No.: 435,118

[22] Filed: May 5, 1995

[51] Int. Cl.⁶ ................................................. A61B 11/02
[52] U.S. Cl. ..................... 600/214; 600/204; 600/215; 600/219; 600/225; 606/205
[58] Field of Search .............................. 600/204, 210, 600/214–16, 219, 226, 224, 223, 225; 606/205, 206

[56] References Cited

U.S. PATENT DOCUMENTS

| 749,811 | 1/1904 | Bernays | 600/215 |
|---|---|---|---|
| 5,183,032 | 2/1993 | Villalta et al. | 600/224 |

Primary Examiner—Beverly M. Flanagan
Attorney, Agent, or Firm—Kinney & Lange, P.A.

[57] ABSTRACT

A surgical retractor retracts tissue from a body cavity in which surgery is to be performed. The retractor has a plurality of fingers or blades which extend laterally from a handle. The fingers pivot about a pivot pin between a retracted position and an extended position. Extension is achieved by rotation of a centered control plate relative to the handle. The pivot pin for the fingers is displaced from the axis of the handle, and moves relative to the handle. Each of the fingers has an arcuate slot, and a guide post within the arcuate slots controls pivoting. Because of the distance separating the pivot pin and the axis of the handle, extension of the fingers occurs a distance away from the incision into which the retractor is inserted, and undue trauma to the incision is avoided. Because the pivot point moves relative to the handle, the fingers extend longitudinally during the pivoting motion. Different lengths, numbers and configurations of blades or fingers may be used to provide the desired profile and continuity for the retraction area.

24 Claims, 10 Drawing Sheets

LAPAROSCOPIC RETRACTOR HAVING A PLURALITY OF BLADES EXTENDING LATERALLY FROM A HANDLE

BACKGROUND OF THE INVENTION

This invention relates generally to surgical instrumentation and, more particularly, to a retractor for use in retracting tissue during a surgical procedure within a body cavity.

Numerous surgical procedures require tissue to be retracted and held away from the site of the surgical procedure. One particular example of this is laparoscopic surgery in which the abdominal wall needs to be retracted from an abdominal body cavity so that a surgical procedure or examination may be effected within the abdominal cavity. Various methods and instrumentation are available to assist in retracting tissue. For example, forceps of various sizes and configurations are used to attach retracted tissue to a separate support (often other tissue) and thereby maintain tissue in a retracted position.

In laparoscopic surgery, one well-known method of retracting the abdominal wall is to insufflate the abdominal cavity with a suitable insufflation gas such as air or carbon dioxide. A significant disadvantage of gas insufflation is that instruments must be passed into the abdominal cavity through gas-tight seals, which significantly reduces the surgeon's dexterity and feel with the instruments.

More recent structures for tissue retraction include a PERITONITAL MECHANICAL RETRACTION APPARATUS AND METHOD OF USING described in PCT/US92/04456, WO 92/21294 of Moll et al., and a SURGICAL RETRACTOR described in U.S. Pat. No. 5,195,505 to Josefsen. The Moll et al. device has two angle shaped retractor elements which extend laterally from a handle. Separate controls are provided at the proximal end of the handle to control pivoting of the two legs relative to each other. The Josefsen device has a plurality of interleaved retractor blades which rotate and fan out along the axis of the handle.

Many surgical procedures require the surgeon to employ the retractor at a location that he or she does not have complete vision. Accordingly, the retractor should be easily and precisely controllable and allow the surgeon to know exactly the extent of the retraction surface without viewing the retractor. The retractor should be designed to minimize trauma to the tissue retracted. None of these known surgical instruments and methods provide the balance, utility and ease of operation which is optimally desired for retracting tissue in a surgical procedure.

SUMMARY OF THE INVENTION

The present invention is a surgical retractor for retracting tissue from a body cavity in which surgery is to be performed. The retractor has a plurality of fingers or blades which extend laterally from a handle. The fingers pivot with respect to a pivot point between a retracted position and an extended position. The pivot point for the fingers is displaced from the axis of the handle. Because of the distance separating the pivot point and the axis of the handle, extension occurs a distance away from the incision into which the retractor is inserted, and undue trauma to the incision is avoided. The fingers also extend longitudinally during the pivoting motion. Different lengths, numbers and configurations of blades may be used to provide the desired profile and continuity for the retraction area. The fingers extend outward in both directions from a central retracted position, and extension is provided by balanced rotation of a control plate.

DETAILED DESCRIPTION OF THE PREFERRED EMBODIMENTS

Figure 1:
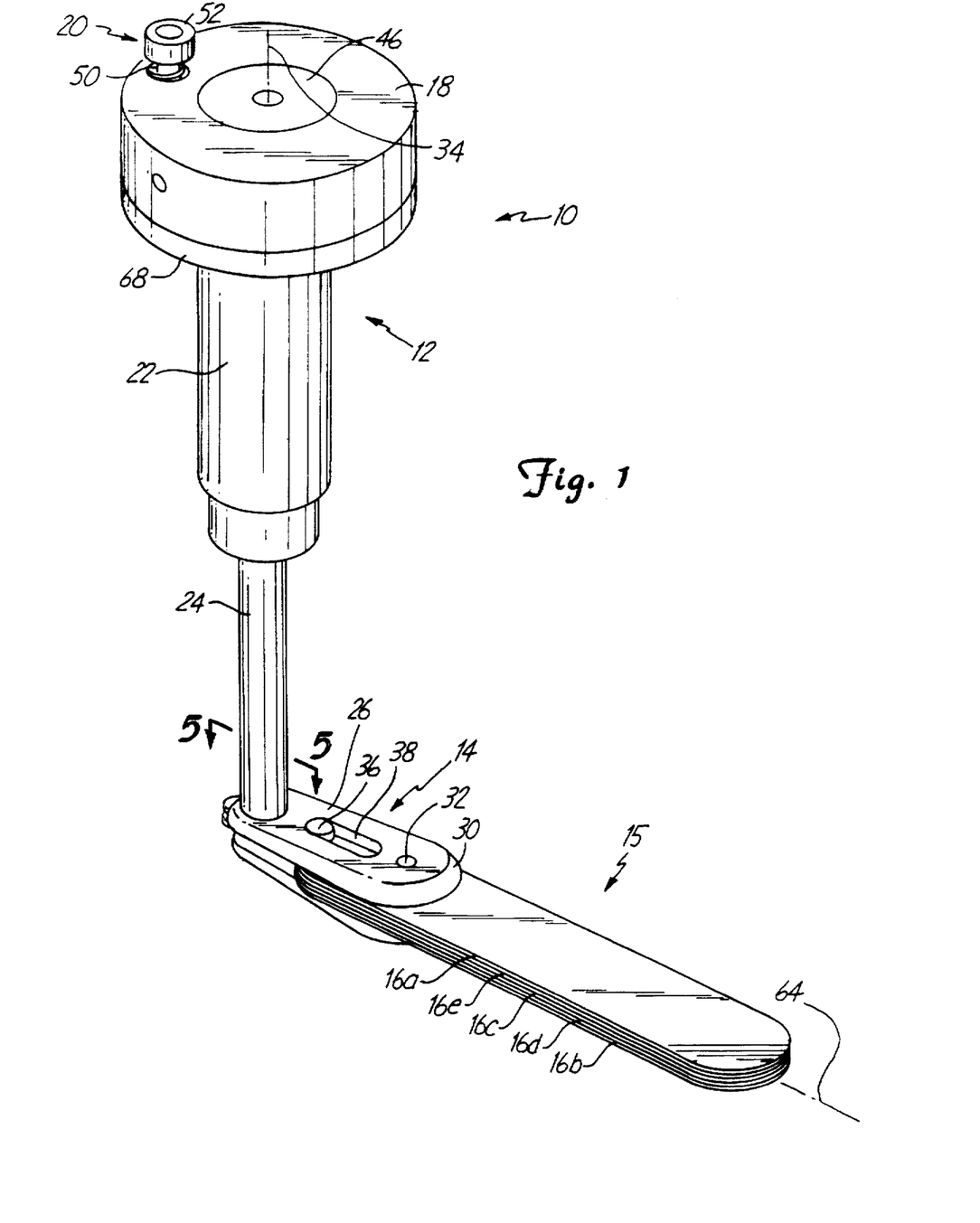
FIG. 1 is a perspective view of the surgical retractor of the present invention with the fingers in a retracted position.

FIG. 1 illustrates the surgical retractor 10 of the present invention in a retracted position. A retractor 10 includes a main body or a handle section 12 and a base section 14. The base section 14 includes a finger assembly 15 which has a plurality of blades or fingers 16a, 16b, 16c, 16d and 16e. The finger assembly 15 is extendable between the retracted position of FIG. 1 and the extended position of FIG. 2. All of the elements may be made of surgical stainless steel or other materials acceptable for use in a surgical setting. The retractor 10 is used by inserting the base section 14 into an incision, extending the finger assembly 15, and the raising the retractor 10 to lift tissue. When the surgical procedure is completed, the finger assembly 15 is retracted, and the retractor 10 is removed.

It should be understood that an "incision", as used herein, refers to an opening in the tissue to be retracted. In situations where an opening or incision exists prior to surgery, the retractor 10 made be directly inserted into the opening and there may be no need to cut the tissue during surgery.

The handle section 12 includes a control plate 18, a detente mechanism 20, a body portion 22 and an extension portion 24. The base section 14 includes a top plate 26 and a bottom plate 28, which are rigidly attached to the extension portion 24 of the handle section 12. The top plate 26 and the bottom plate 28 preferably have a smoothly rounded edge 30 without any sharp corners. As shown, the top plate 26 and the bottom plate 28 preferably extend longitudinally for a short distance along the finger assembly 15. A guide post 32 rigidly attaches to the top plate 26 and the bottom plate 28, preferably at a location away from axis 34 of the handle section 12. A pivot pin 36 is slidably received within a slot 38 of the top plate 26. A similar slot 40 (see FIGS. 3 and 4) may be provided in the bottom plate 28 to slidably receive the pivot pin 36.

Figure 2:
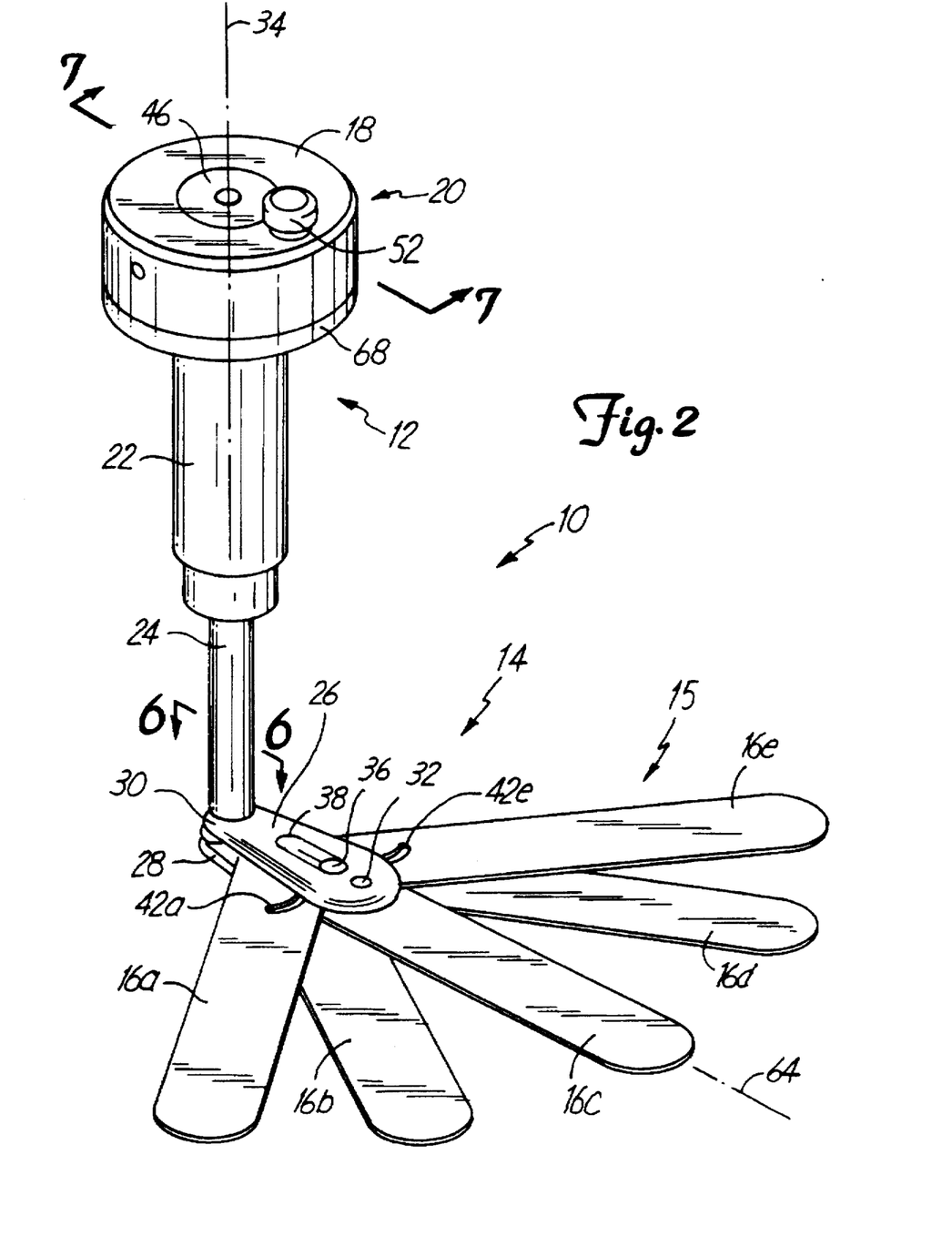
FIG. 2 is a perspective view of the surgical retractor of the present invention with the fingers in an extended position.

To extend the finger assembly 15 as illustrated in FIG. 2, the control plate 18 is rotated 180° with respect to the body portion 22 (evidenced by the location of the detente mechanism 20). During extension, the pivot pin 36 moves outward from the axis 34 within the slot 38. Arcuate slots 42a and 42e are shown within the blades 16a and 16e, respectively. The operation of the pivot pin 36, the arcuate slots 42a through 42e and the guide post 32 in extending the finger assembly 15 will be described below with reference to FIGS. 4–6.

Figure 3:
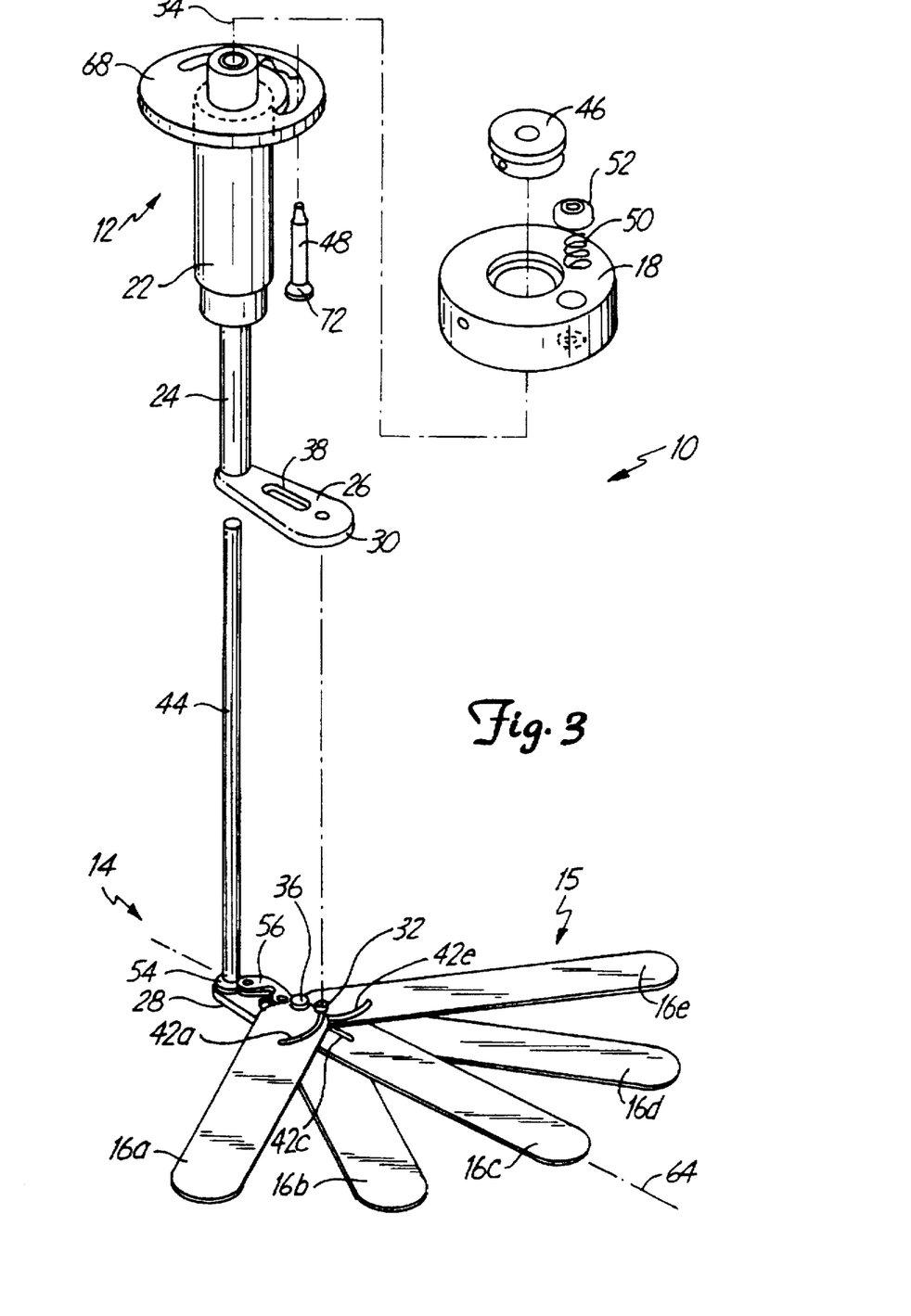
FIG. 3 is an exploded perspective view illustrating assembly of the retractor.

FIG. 3 illustrates an exploded view indicative of assembly of the retractor 10. A shaft 44 projects into the extension portion 24 and the body portion 22 and is rotatably received therein. The control plate 18 is rigidly attached to the shaft 44 by a cap 46, such that rotation of the control plate 18 with respect to the body portion 22 causes the shaft 44 to rotate within the body portion 22. The detente mechanism 20 includes a plunger 48, a spring 50, and a thumb release 52. The detente mechanism 20 releasably secures the control plate 18 (and the shaft 44) from rotation within the body portion 22. The specific operation of the detente mechanism 20 will be further described below with reference to FIGS. 7 and 8.

Figure 4:
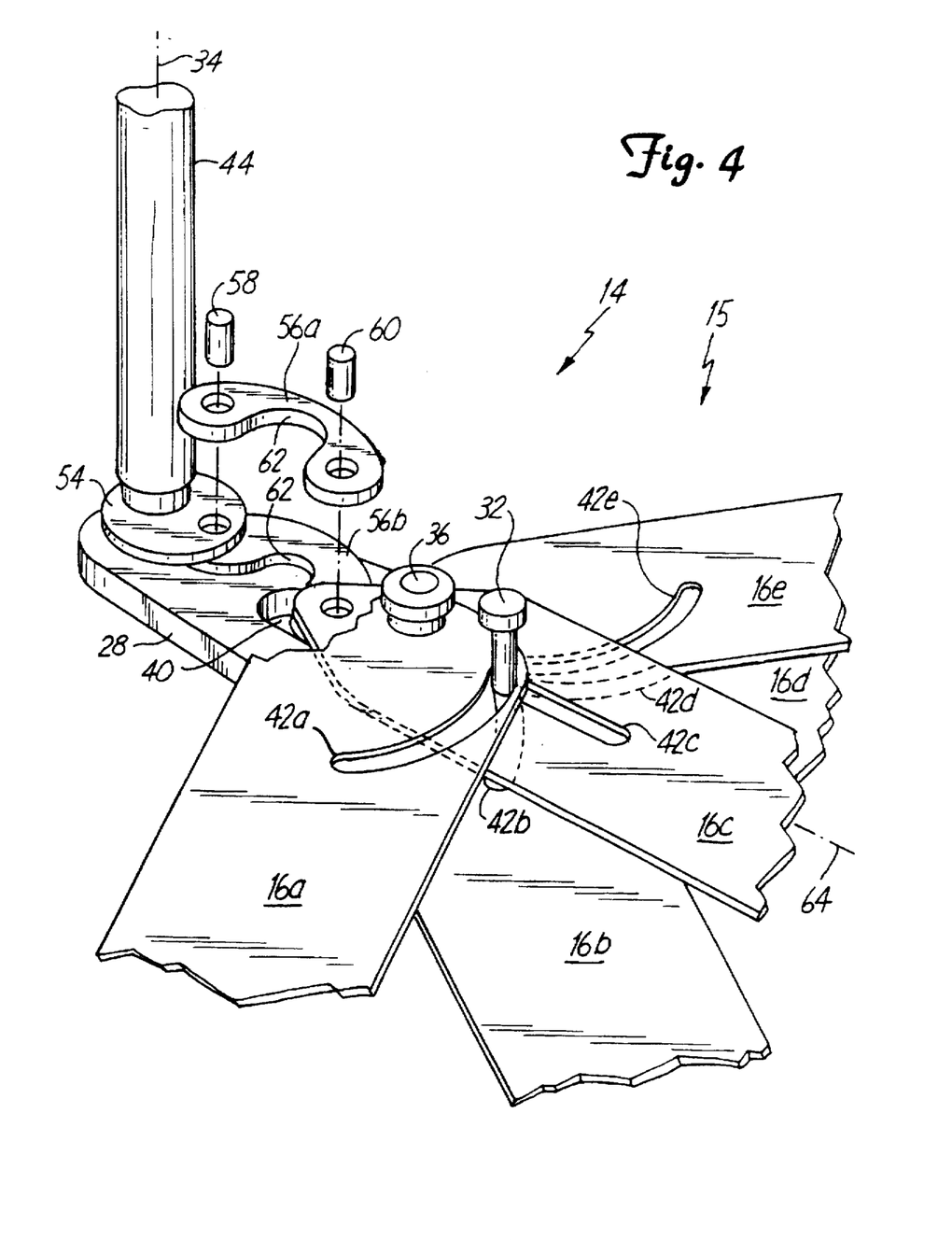
FIG. 4 is an expanded exploded perspective view illustrating assembly of the base of the retractor.

FIG. 4 is an expanded view of the base section 14 with the upper plate 26 removed. A cam 54 is rigidly attached to the shaft 44. The cam 54 is pivotally connected to a link 56 at a pin 58. The link 56 includes an upper portion 56a and a lower portion 56b, both of which have a curved section 62. The link 56 is pivotally connected to the center blade 16c at a pin 60. A portion of the slot 40 for the pivot pin 36 can be seen in tile lower plate 28.

The pivot pin 36 pivotally connects the center blade 16c to the remaining blades 16a, 16b, 16d and 16e. The pivot pin 36 is preferably oriented to provide a pivoting axis for the blades 16a, 16b, 16c, 16d and 16e which is parallel to axis 34. As illustrated ill FIG. 4, each of the blades 16a, 16b, 16c, 16d and 16e has a slot 42a, 42b, 42c, 42d and 42e which may be arcuate with the desired contour, and the guide post 32 extends through the slots 42a, 42b, 42c, 42d and 42e. By having the slots 42a, 42b, 42d and 42e be arcuate, the guide post 32 causes tile outside blades 16a, 16b, 16d and 16e to pivot about the pivot pin 36 during extension of the finger assembly 15. The slot 42c in the center blade 16c may be straight. By having the slot 42c be straight, extension of the finger assembly 15 causes the center blade 16c to project along a longitudinal axis 64 outwardly without pivoting.

Figure 5:
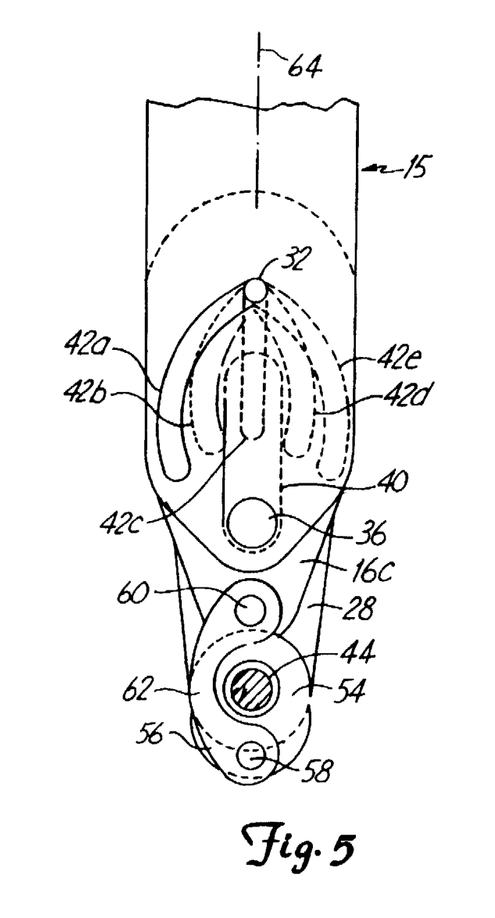
FIG. 5 is a cross-sectional view taken along line 5—5 of FIG. 1 with the top plate removed.
Figure 6:
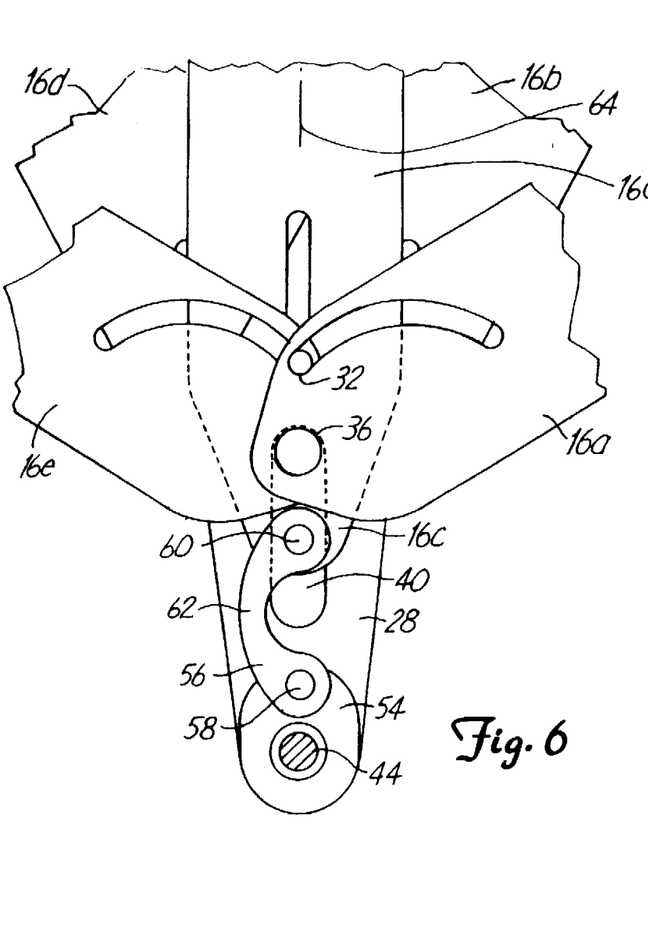
FIG. 6 is a cross-sectional view taken along line 6—6 of FIG. 2 with the top plate removed.

In the retracted position of FIG. 5, the guide post 32 is at the distal end of the slots 42a, 42b, 42c, 42d and 42e, and the pivot pin 36 is at the proximal end of the slot 40. As can be seen, the link 56 with the curved section 62 wraps around the shaft 44. If the shaft 44 and cam 54 are turned counterclockwise, the curved section 62 will butt up against the shaft 44, preventing further rotation. In this way, the shaft 44 provides a stop for the link 56, so that the surgeon knows the finger assembly 15 is located in the retracted position without having to view the device.

Through the cam 54, clockwise rotation of the shaft 44 causes the link 56 to push the center blade 16c longitudinally outward. The guide post 32 within the slot 42c and the pivot pin 36 within the slots 38, 40 assure that the center blade 16c does not pivot as it is pushed longitudinally outward. The pivot pin 36 carries the remaining blades 16a, 16b, 16d and 16e with it as it moves longitudinally outward. The guide post 32 extends into and bears against the arcuate slots 42a, 42b, 42d, 42e to force the outside blades 16a, 16b, 16d and 16e to pivot about the moving pivot pin 36. In the fully extended position of FIG. 6, the guide post 32 is at the proximal end of the slots 42a, 42b, 42c, 42dand 42e, and the pivot pin 36 is at the distal end of the slot 40.

Workers skilled in the art will appreciate that a wide array of structures may be included in the linkage to move the pivot pin 36. For instance, the cam 54 could be replaced by a short link welded or otherwise attached to the shaft 44, without need for a circular cam. However, the circular configuration of the cam 54 lends balance to the extension and retraction of the retractor 10. The circular configuration or the cam 54 also provides a mechanical advantage adjacent the fully extended and fully retracted positions, wherein significant rotation of shaft the 44 will provide only a small change in position of the pivot point 36. Thus the surgeon can have a more delicate touch in using the retractor 10.

Figure 7:
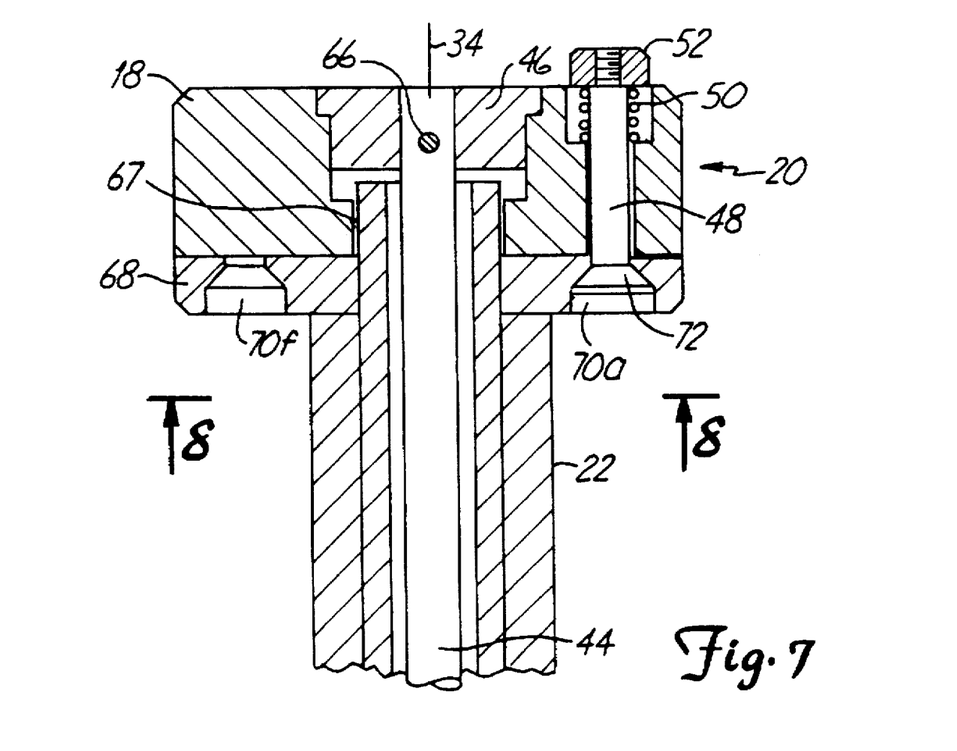
FIG. 7 is a cross-sectional view taken along line 7—7 of FIG. 2.
Figure 8:
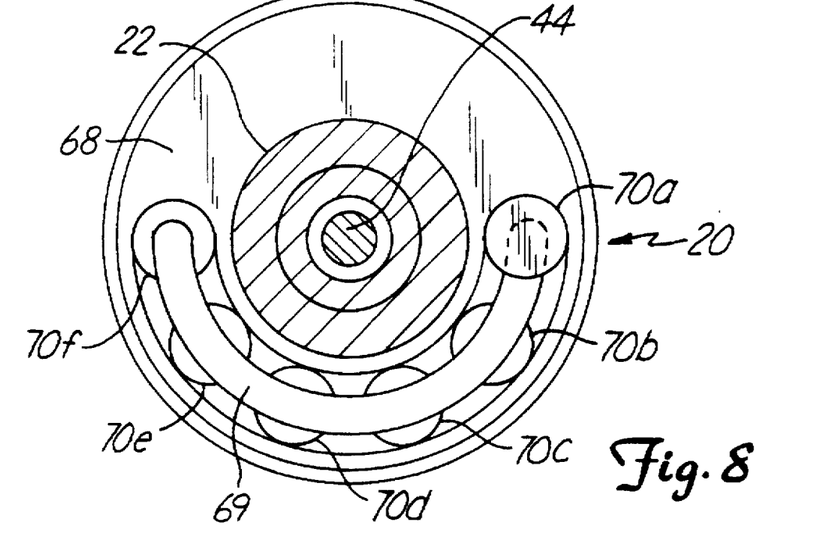
FIG. 8 is a cross-sectional view taken along line 8—8 of FIG. 7.

FIGS. 7 and 8 are cross-sectional views illustrating attachment of the control plate 18 to the body portion 22. The shaft 44 is rigidly attached to the end cap 46 by a set screw 66, and the end cap 46 is rigidly attached to the control plate 18. The control plate 18 has a bearing surface 67 which bears against the proximal end of the body portion 22 to maintain the axial relationship of the control plate 18 and the body portion 22.

A detente plate 68 is rigidly attached to the body portion 22. The detente plate 68 has a plunger channel 69 with six detente recesses 70a, 70b, 70c, 70d, 70e and 70f defined therein. When secured in the fully extended position by the detente mechanism 20, head 72 of the plunger 48 is within the detente recess 70a and prevents rotation of the control plate 18 relative to the body portion 22. By depression of the thumb release 52, the head 72 of the plunger 48 can be removed from any of the detente recesses 70a, 70b, 70c, 70d, 70e, 70f, and rotation of the control plate 18 relative to the body portion 22 is possible. The plunger channel 69 extends around approximately 180° of the detente plate 68, and provides a stop to prevent further rotation of the control plate 18 relative to the body portion 22. The ends of the plunger channel 69 match the points of full extension and full retraction of the finger assembly 15. Workers skilled in the art will appreciate that various other types of detente mechanisms will suitably prevent extension or retraction of the finger assembly 15 unless desired by the surgeon.

Figure 9:
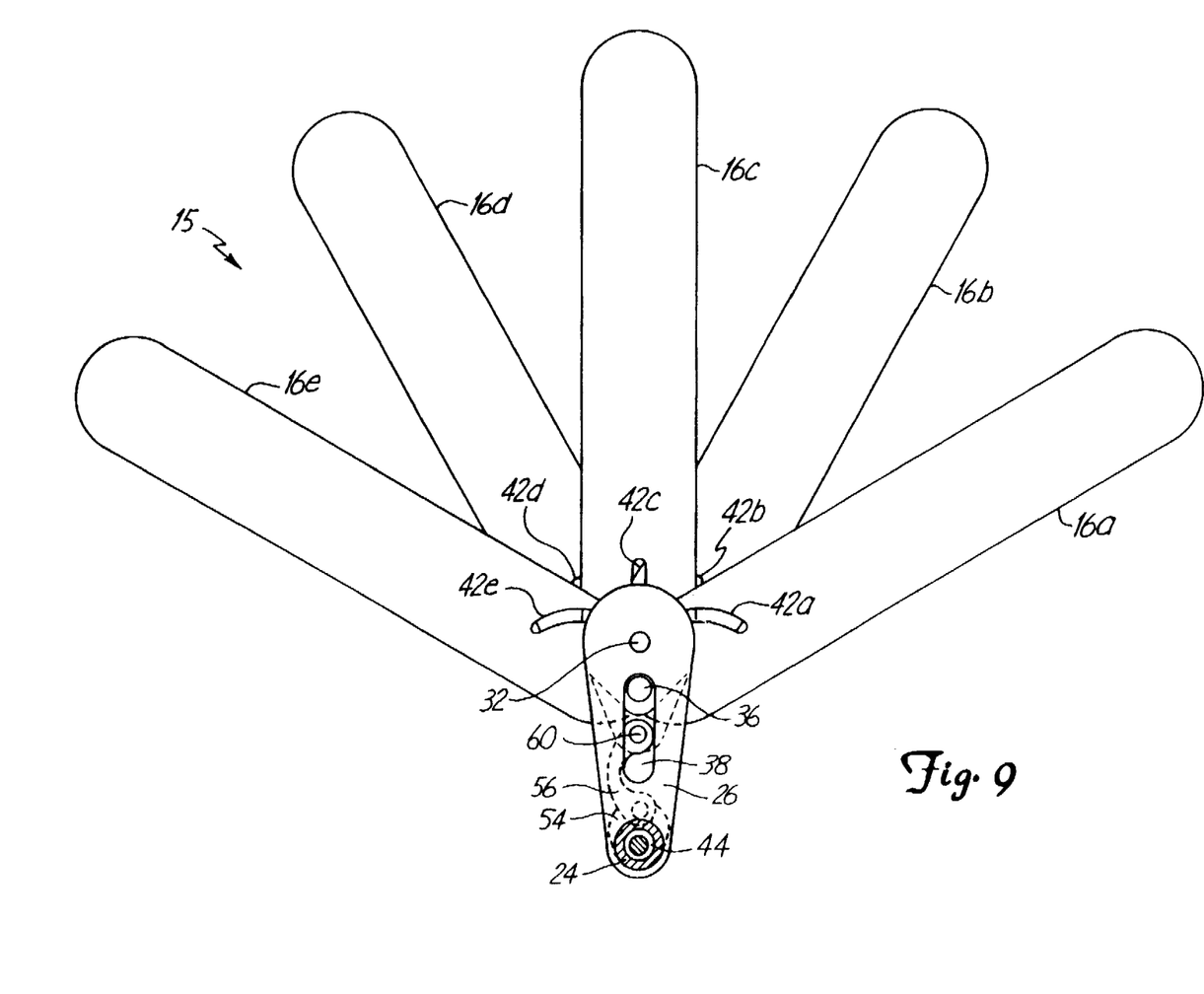
FIG. 9 is a plan view of the blade configuration in the extended position.

FIG. 9 illustrates a plan view of the first blade configuration for the present invention. During extension of the finger assembly 15, two blades 16a and 16b pivot away from the right side of the center blade 16c, and two blades 16d and 16e pivot away from the left side of the center blade 16c. The arcuate slots 42a through 42e each have a different configuration, and the amount of pivoting can be separately controlled for each blade 16a, 16b, 16c, 16d and 16e as desired. With this first blade configuration, the outermost blades 16a and 16e pivot about 60° from the longitudinal axis 64 when fully extended, and the intermediate blades 16b and 16d pivot about 30° from the longitudinal axis 64 when fully extended. The pivoting of the outside blades 16a, 16b, 16d and 16e occurs symmetrically and simultaneously. However, the contour and shape of the slots 42a, 42b, 42c, 42d and 42e may be chosen to provide differing rates and amounts of pivoting for each blade 16a, 16b, 16c, 16d and 16e if desired.

Figure 10:
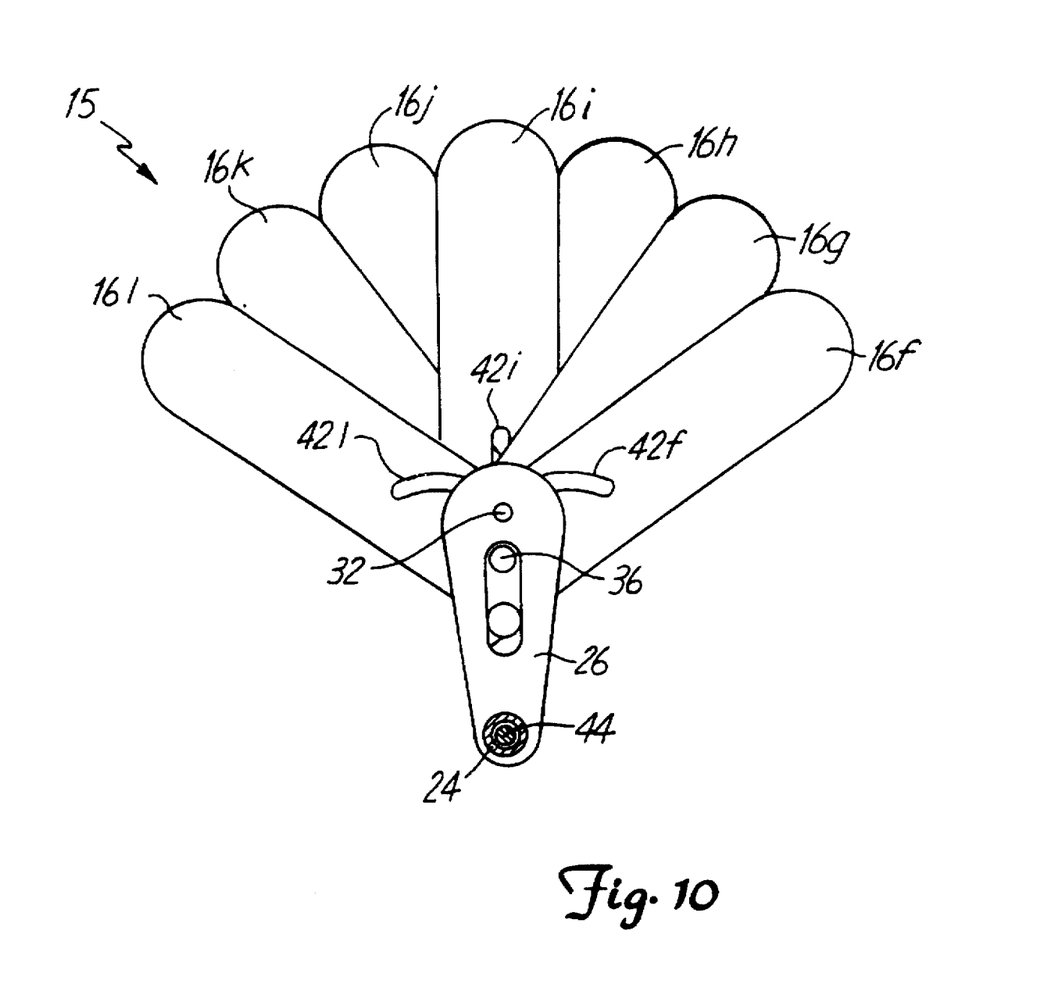
FIG. 10 is a plan view of an alternative blade configuration in the extended position.

An alternative blade configuration for the present invention is illustrated in FIG. 10. In this alternative blade configuration, seven blades 16f, 16g, 16h, 16i, 16j, 16k and 16l are provided. These blades 16f through 16l are all the same length as each other, but are somewhat shorter and narrower than the blades 16a through 16e of the of the first blade configuration. Each of the blades 16f through 16l has an outside profile identical to the other blades 16f through 16l, and the pivoting of blades 16f through 16l occurs symmetrically and simultaneously. When fully extended, the seven blades 16f through 16l make up a substantially continuous retraction surface which extends over about a 110° arc.

Figure 11:
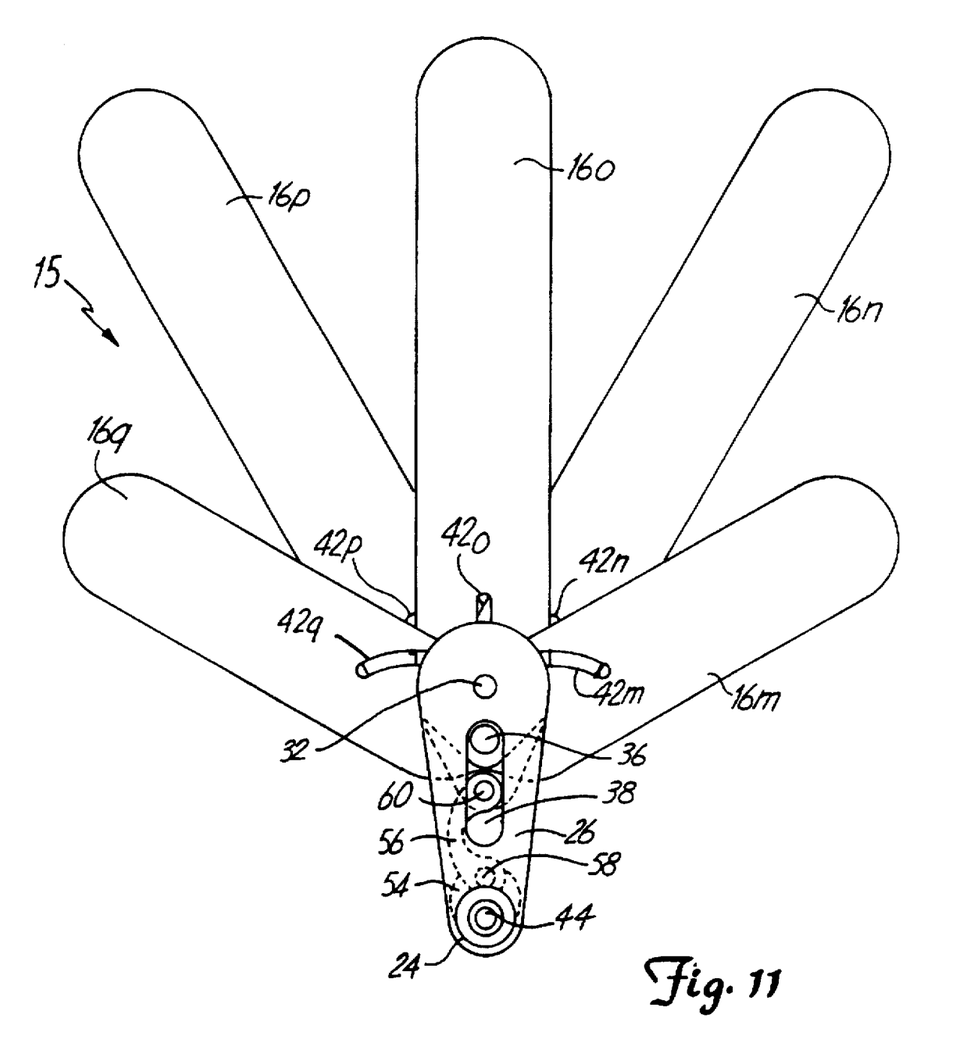
FIG. 11 is a plan view of a second alternative blade configuration in the extended position.

A second alternative blade configuration for the present invention is illustrated in FIG. 11. The outermost blades 16m and 16q are somewhat shorter, and the intermediate blades 16n and 16o are slightly longer as compared to the center blade 16p. This provides for a retraction surface which is somewhat rectangular in profile as compared to the wedged-shaped retraction surface of the blades 16f through 16l of the alternative blade configuration shown in FIG. 10.

Based on this disclosure, workers skilled in the art will readily appreciate that the length of the blades, the shape of the blades, and the shape of the bearing slots can be controlled for any particular application to develop the retraction surface profile desired. While flat blades are shown, workers skilled in the art will appreciate that other configurations and cross-sectional shapes of fingers or blades may be used. For instance, the fingers could be circular rather than flat, or have a cross-sectional contour which changes longitudinally. As another example, plastic may be used for the finger sections to allow for less strength and more bending of the fingers during retraction of the tissue.

Figure 12:
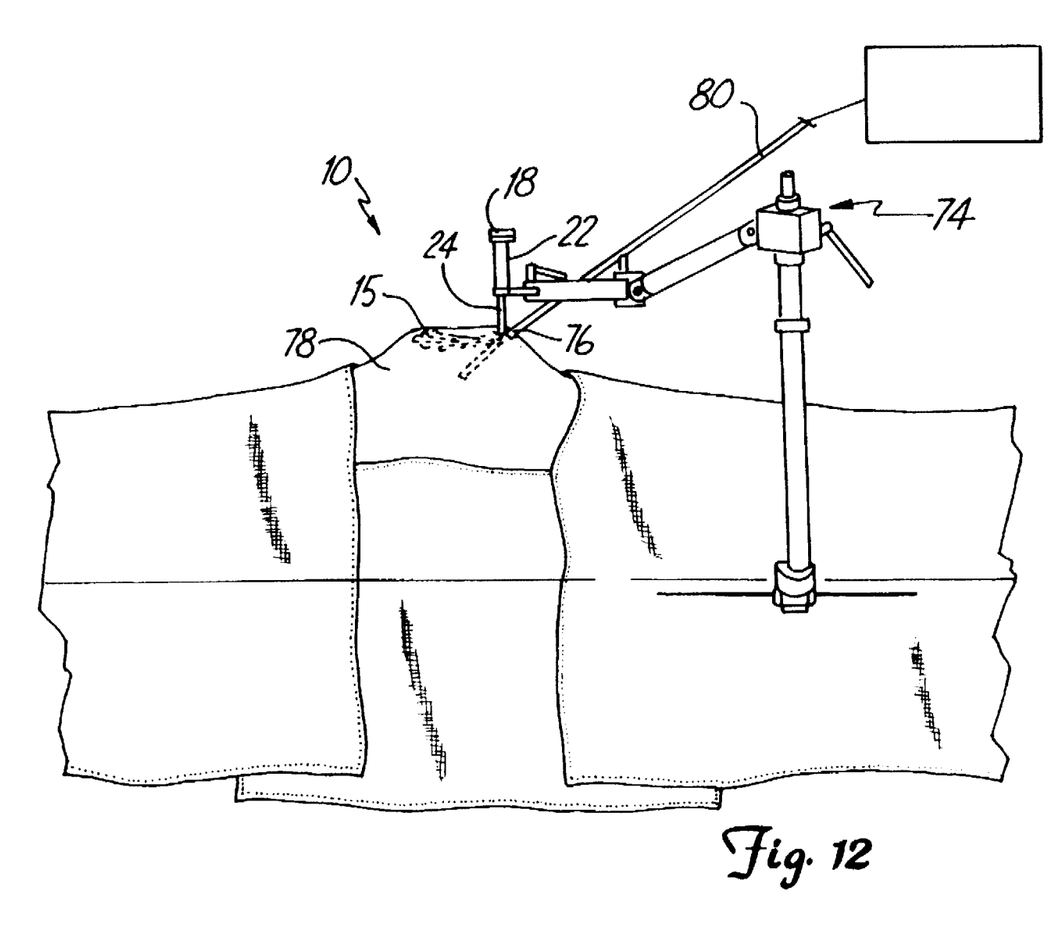
FIG. 12 is a side view illustrating use of the surgical retractor in a patient.

Use of the retractor 10 of the present invention is illustrated in FIG. 12. First, an incision 76 is provided through tissue 78. The base section 14 of the retractor 10 is inserted into the incision 76 by angling and extending the finger assembly 15 along the tissue 78 to be retracted while in the retracted position. For instance, the finger assembly 15 may extend between the abdominal wall and the underlying organs. After insertion of the base section 14 through the incision 76, the surgeon depresses the thumb release 52 of the detente mechanism 20 and rotates the control plate 18 an appropriate amount for the desired extension of the finger assembly 15. Once the desired extension is obtained, the thumb release 52 is released, such that the detente mechanism 20 maintains the finger assembly 15 in the extended position. The retractor 10 is lifted along its axis 34 to retract the tissue 78. At this point, a mechanical arm 74 may be arranged and situated to hold the retractor 10 at the desired elevation. Other surgical tools 80 may be used as desired on the underlying organs in the space provided by the retracted tissue 78. Upon completion of the surgical procedure, the retractor 10 is lowered along its axis 34 until the tissue 78 is back in place. The surgeon depresses the thumb release 52 of the detente mechanism 20 and rotates the control plate 18 to fully retract the finger assembly 15. Once in the fully retracted position, the base section 14 is removed from the incision 76.

The present invention provides numerous advantages over the prior art retractors. First, because the blades extend generally perpendicular to the axis of the main handle portion, lifting of the tissue may be easily accomplished merely by lifting the handle along its axis. The retractor handle extends through the incision in a direction substantially normal to the retractor blades. One side of the incision does not have to be raised or lowered during lifting of the tissue with respect to the other side of the incision, preventing undue trauma to the incision location.

With at least three finger sections, the retractor can provide a substantially continuous retraction surface, or can provide retraction pressure along numerous different fingers. Controlled extension of all of the finger sections is accomplished with ease by the surgeon by rotating the control plate with respect to the handle, and it is not necessary for the surgeon to separately manipulate controls for each of the finger sections. The detente mechanism allows the surgeon to determine the amount of extension of the retractor blades and to easily maintain the retractor at the determined amount of extension without worry of the force of the tissue forcing the retractor blades inward.

The detente mechanism and the stop of link 56 also allows the surgeon to be sure that the retractor is completely in its retracted position without vision of the retractor blades. The surgeon avoids removing the retractor through the incision while any of the blades are extended, which could cause unnecessary damage to the incision location.

The present invention has retractor blades which extend from both sides of a central retracted position. This prevents an undue buildup of strain or tension on the tissue being retracted. Having blades extend from both sides of the retracted position further aids the surgeon in manipulation of the retractor, as the force opposing extension of the retractor blades generally will be equal from both sides. In this way, the surgeon has a tool which is maintains a balance of forces during use, and the surgeon does not have to place an outside force in one direction or the other during extension of the retractor.

The circular control plate, centered on the handle axis, similarly allows the surgeon to extend the retractor blades while placing no net force or moment on the retractor. Centering of the control plate helps provide more delicate feel and control by the surgeon. During extension and retraction of the retractor, all the surgeon need do is depress the thumb release of the detente mechanism and provide a balanced rotational force on the control plate.

The arcuate slots in each of the blades may be configured as necessary for many different applications. For instance, by providing a different arc between the same opening and end positions, the design of the retractor may be controlled such that one blade extends only during the beginning of the retractor extension, while a different blade extends only during the end of the retractor extension. A straight slot between the same opening and end positions will provide a differing rate or blade extension. The amount of longitudinal extension versus pivoting of each blade is thus entirely determined by the contour of the arc. Retractors may be designed as desired to control both the amount of longitudinal extension and the amount of pivoting of each blade separately. Similarly, while the profiles of the blades shown are symmetrical, it will be appreciated that the blade configuration does not have to be symmetrical. The blades along one side of the retractor may be longer or shaped differently than the blades on the other side of the retractor to provide a non-symmetrical retraction surface.

The fingers of the present invention not only pivot, but also extend along the longitudinal axis during extension of the retractor. Each of the distal ends of the fingers may be located further from the axis of the handle in an extended state than it is in a retracted state. Thus, the retraction surface is not only wider, but also longer in the extended position than in the retracted position. Because the distal ends of the fingers are closer to the axis of the handle in the retracted position, insertion of the retractor into the incision is easier. Both the longitudinal and the pivotal extension is accomplished by movement of the pivot point with respect to the handle.

The pivot point of the retractor of the present invention is not necessarily located along the axis of the handle section. By displacing the pivot point from the axis of the handle section, the blade extension occurs more remotely from the incision in tile tissue. The forces that the retractor places on the tissue while the tissue is being lifted also occur at a location displaced from the incision. Displacing forces from the incision location helps to prevent additional tearing or undue trauma to the incision location.

The guide post may be located remotely from the axis of the handle. However, if the retraction surface is desired to include the incision, the guide post could be located at the axis of the handle so the retraction surface is centered on the incision location. However, the design shown and described permits the retractor to expand away from the incision rather than immediately adjacent the incision.

The top and bottom plate at the base of the retractor may have an edge contour which is different from the contour of the blades. By having a rounded contour as shown, tile top and bottom plate help to avoid injury or trauma to the area around the incision. The top and bottom plates may be dimensioned as desired and do not have to be the size shown. For instance, the plates may cover the entire surface of the retractor blades in the retracted condition.

Although the present invention has been described with reference to preferred embodiments, workers skilled in the art will recognize that changes may be made in form and detail without departing from the spirit and scope of the invention. For instance, the finger sections described here are substantially in the same plane both in the retracted and the extended positions. However, if the retraction surface is desired to have a contour, the fingers may project in different planes or pivot about axes which are slightly angled with respect to each other. In this way, the retractor described may readily be modified to have finger sections which project substantially along different planes or have finger sections which, though projecting in a single plane when inserted, extend into different planes when the retractor is extended.

As another example, the retractor can be readily modified such that the axis of the pivot pin is not parallel to the axis of the handle, thereby provide a retraction surface which is not substantially normal to the axis of the handle. Various base sections may be substituted with a single retractor handle if desired, or multiple retractors may be provided, such that the surgeon may choose the desired retraction surface profile or any particular operation.

As another example, workers skilled in the art will appreciate that other types of bearing guides other than a post could be used for the present invention. For instance, the blades may have a bearing contour on one or more outside surfaces of the blades to control pivoting. Workers skilled in the art will recognize that numerous additional changes may be made in form and detail without departing from the spirit and scope of the invention.

What is claimed is:

1. A retractor for retracting tissue when performing endoscopic or laparoscopic surgical techniques, the retractor comprising:

a main body portion having a central axis;

a plurality of retractor blades mounted for pivoting with respect to the main body portion, wherein the retractor blades project from the main body portion substantially perpendicular to the central axis and wherein the retractor blades are pivotable about a pivot axis that is parallel to and offset from the central axis;

a cam mechanism operably connecting the retractor blades to the main body portion; and a rod mounted within the main body portion so that the rod is rotatable about the central axis, wherein the rod engages the cam mechanism so that rotation of the rod causes the retractor blades to move between a retracted position and an extended position.

2. The retractor of claim 1, wherein the plurality of retractor blades comprises:

a first retractor blade having a first length; and a second retractor blade having a second length, wherein the first length is different than the second length.

3. The retractor of claim 1, wherein the cam mechanism comprises:

a cam attached to the rod; and a link operably connecting the cam to the retractor blades.

4. The retractor of claim 3 and further comprising:

a control plate attached to the rod opposite the cam; and a detente mechanism operably engaging the control plate, wherein the detente mechanism is capable of maintaining the retractor blades in a selected position.

5. The retractor of claim 1, wherein the plurality of retractor blades comprises a first retractor blade, wherein the first retractor blade has a bearing contour defined thereby, and wherein the retractor further comprises:

a pivot point movably attached to the main body portion, wherein the first retractor blade is pivotally attached to the pivot point; and a bearing guide attached to the main body portion, wherein the bearing guide translates movement of the pivot point into pivoting of the first retractor blade.

6. The retractor of claim 5, wherein the bearing contour comprises an arcuate slot, and wherein the bearing guide comprises a post within the slot.

7. A retractor for retracting tissue, the retractor comprising:

a main body portion having a central axis;

a plurality of retractor blades projecting from the main body portion substantially perpendicular to the central axis, wherein the retractor blades are pivotable about a pivot axis that is parallel to and offset from the central axis;

a rod mounted within the main body portion so that the rod is rotatable about the central axis, wherein the rod operably engages the retractor blades; and a control plate secured to the rod, wherein rotation of the control plate causes rotation of the rod and wherein rotation of the rod causes the retractor blades to move between a retracted position and an extended position.

8. The retractor of claim 7, wherein each of the retractor blades are substantially flat, and wherein the retractor blades act together to provide a substantially continuous surface when the retractor blades are in the extended position.

9. The retractor of claim 7, and further comprising a detente mechanism operably engaging the control plate, wherein the detente mechanism is capable of maintaining the retractor blades in a selected position.

10. The retractor of claim 7, wherein the plurality of retractor blades comprises a first retractor blade, wherein the first retractor blade has a bearing contour defined thereby, and wherein the retractor further comprises:

a pivot point movably attached to the main body portion, wherein the first retractor blade is pivotally attached to the pivot point; and a bearing guide attached to the main body portion, wherein the bearing guide translates movement of the pivot point into pivoting of the first retractor blade.

11. The retractor of claim 10, wherein the bearing contour comprises an arcuate slot, and wherein the bearing guide comprises a post within the arcuate slot.

12. The retractor of claim 10, and further comprising means for remotely moving the pivot point with respect to the handle.

13. The retractor of claim 12, wherein the means for remotely moving the pivot point comprises:

a linkage having a first end and a second end, wherein the first end is attached to the pivot point and wherein the second end is attached to the main body portion.

14. The retractor of claim 12, wherein the mean for remotely moving the pivot point comprises:

a rod mounted within the main body portion so that the rod is rotatable about the central axis;

a cam attached to the rod;

a link operably connecting the cam to the retractor blades; and a control plate attached to the rod opposite the cam.

15. A method of retracting tissue with a retractor when performing endoscopic or laparoscopic surgical techniques, the retractor having a main body portion with a central axis and a plurality of retractor blades projecting from the main body portion substantially perpendicular to the central axis, the method comprising:

positioning the retractor blades in a retracted position;

inserting the retractor blades through an incision in the tissue;

rotating a rod mounted within the main body portion about the central axis, wherein the rod is operably connected to the retractor blades with a cam mechanism so that rotation of the rod moves the retractor blades the to extended position; and lifting the main body portion along the central axis to retract the tissue.

16. The method of claim 15, wherein the retractor blades act together to provide a substantially continuous surface when the retractor blades are pivoted to the extended position.

17. The method of claim 15, wherein the retractor blades pivot about a pivot axis that is parallel to and offset from the central axis when moving from the retracted position to the extended position.

18. The method of claim 15, wherein the cam mechanism comprises:

a cam attached to the rod; and a link operably connecting the cam to the retractor blades.

19. The method of claim 15, wherein the retractor further comprises a control plate secured to the rod, wherein the method further comprises:

engaging the control plate with a detente mechanism to retain the retractor blades in a selected position.

20. The method of claim 15, wherein the retractor further comprises a pivot point to which the retractor blades are pivotally attached, wherein the method further comprises:

moving the pivot point with respect to the main body portion to thereby extend the retractor blades.

21. A method of retracting tissue with a retractor, the retractor having a main body portion with a central axis and a plurality of retractor blades projecting from the main body portion substantially perpendicular to the central axis, the method comprising:

positioning the retractor blades in a retracted position;

inserting the retractor blades through an incision in the tissue;

rotating a rod mounted within the main body portion about the central axis, wherein the rod is operably connected to the retractor blades;

pivoting the retractor blades about a pivot axis that is parallel to and offset from the central axis to cause the retractor blades to pivot from the retracted position to an extended position; and lifting the main body portion along the central axis to retract the tissue.

22. The method of claim 21, wherein the retractor further comprises a cam attached to the rod and a link operably connecting the cam to the retractor blades, and wherein rotation of the rod causes the cam to rotate, and wherein rotation of the cam causes the link to pivot the retractor blades between the retracted position and the extended position.

23. The method of claim 21, wherein the retractor further comprises a control plate secured to the rod, wherein the method further comprises:

engaging the control plate with a detente mechanism to retain the retractor blades in a selected position.

24. The method of claim 21, wherein the retractor further comprises a pivot point to which the retractor blades are pivotally attached, wherein the method further comprises:

moving the pivot point with respect to the main body portion to thereby extend the retractor blades.

* * * * *

UNITED STATES PATENT AND TRADEMARK OFFICE
CERTIFICATE OF CORRECTION

PATENT NO. : 5,722,935

DATED : MARCH 3, 1998

INVENTOR(S) : STEVEN C. CHRISTIAN

It is certified that error appears in the above-identified patent and that said Letters Patent is hereby corrected as shown below:

Col. 3, Line 28, delete "tile" and insert --the--

Col. 3, Line 34, delete "ill" and insert --in--

Col. 3, Line 39, delete "tile" and insert --the--

Col. 3 Line 55, delete "clockwise"

Col. 3, Line 66, delete "42dand" and insert --42d and--

Col. 4, Line 8, delete "or" and insert --of--

Col.5, Line 3, delete "are" and insert --arc--

Col. 5, Line 4, delete "tile" and insert --the--

Col. 5, Line 13, delete "tile" and insert --the--

Col. 5, Line 21, delete "fiat" and insert --flat--

Col. 5, Line 40, delete "I0" and insert --10--

Col. 5, Line 62, delete "tile" and insert --the--

Col. 5, Line 67, delete "tile" and insert --the--

Col. 6, Line 18, delete "tile" and insert --the--

UNITED STATES PATENT AND TRADEMARK OFFICE
CERTIFICATE OF CORRECTION

PATENT NO. : 5,722,935  Page 2 of 4

DATED : MARCH 3, 1998

INVENTOR(S) : STEVEN C. CHRISTIAN

It is certified that error appears in the above-identified patent and that said Letters Patent is hereby corrected as shown below:

Col. 6, Line 36, delete "tile" and insert --the--

Col. 6, Line 41, delete "or" and insert --of--

Col. 6, Line 45, delete "tile" and insert --the--

Col. 6, Line 46, delete "tile" and insert --the--

Col. 6, Line 47, delete "tile" and insert --the--

Col. 6, Line 57, delete "tile" and insert --the--

Col. 6, Line 67, delete "tile" and insert --the--

Col. 7, Line 1, delete "tile" and insert --the--

Col. 7, Line 15, delete "tile" and insert --the--

Col. 7, Line 43, delete "or" and insert --for--

UNITED STATES PATENT AND TRADEMARK OFFICE
CERTIFICATE OF CORRECTION

PATENT NO. : 5,722,935
DATED : MARCH 3, 1998
INVENTOR(S) : STEVEN C. CHRISTIAN

It is certified that error appears in the above-identified patent and that said Letters Patent is hereby corrected as shown below:

Title Page, [56] References Cited U.S. PATENT DOCUMENTS insert --

| Pat. No. | Date | Name | Class/Subclass |
|---|---|---|---|
| 5,195,505 | 3/23/93 | Josefsen | 128/20 |
| 5,195,506 | 3/23/93 | Hulfish | 128/20 |
| 5,339,801 | 8/1994 | Poloyko et. al | 600/214 |
| 5,325,848 | 7/1994 | Adams et. al | 600/204 |
| 5,293,863 | 3/1994 | Zhu et. al | 128/20 |
| 5,271,385 | 12/1993 | Bailey | 600/214 |
| 5,199,419 | 4/1993 | Remiszewski et. al | 128/20 |
| 5,152,279 | 10/1992 | Wilk | -/- |
| 5,209,747 | 5/1993 | Knoepfler | 606/205 |
| 5,490,819 | 2/1996 | Nicholas et. al | 606/205 |

UNITED STATES PATENT AND TRADEMARK OFFICE
CERTIFICATE OF CORRECTION

PATENT NO. : 5,722,935
DATED : MARCH 3, 1998
INVENTOR(S) : STEVEN C. CHRISTIAN

It is certified that error appears in the above-identified patent and that said Letters Patent is hereby corrected as shown below:

Title Page, FOREIGN PATENT DOCUMENTS, insert --

| | | | |
|---|---|---|---|
| WO 92/21291 | 12/10/92 | United States-PCT | -/- |
| WO 92/21294 | 12/10/92 | United States-PCT | -/- -- |

Signed and Sealed this

Twenty-ninth Day of June, 1999

Attest:

Q. TODD DICKINSON

*Attesting Officer*      *Acting Commissioner of Patents and Trademarks*